United States Patent [19]

Hinnenkamp

[11] 4,435,598

[45] Mar. 6, 1984

[54] PROCESS FOR THE CATALYTIC OXIDATION OF PROPYLENE TO ACRYLIC ACID

[75] Inventor: James A. Hinnenkamp, Cincinnati, Ohio

[73] Assignee: National Distillers and Chemical Corporation, New York, N.Y.

[21] Appl. No.: 846,470

[22] Filed: Oct. 28, 1977

[51] Int. Cl.³ .................... C07C 51/25; C07C 51/50; C07C 57/045; C07C 57/075
[52] U.S. Cl. .................................. 562/546; 260/413; 562/412; 562/415; 562/543; 562/544; 562/545; 562/547; 562/548; 568/478
[58] Field of Search ................... 260/533 N; 562/546, 562/545, 547

[56] References Cited

U.S. PATENT DOCUMENTS

| | | | |
|---|---|---|---|
| 2,026,894 | 1/1936 | Blackley | 260/526 N |
| 2,105,284 | 1/1938 | Groll et al. | 260/526 N |
| 2,469,701 | 5/1949 | Redmon | 260/526 N |
| 2,485,510 | 10/1949 | Redmon | 260/526 N |
| 3,671,582 | 6/1972 | David et al. | 562/546 |

FOREIGN PATENT DOCUMENTS 1362068  7/1974  United Kingdom ........... 260/533 N

*Primary Examiner*—Vivian Garner
*Attorney, Agent, or Firm*—Kenneth D. Tremain

[57] ABSTRACT

An improved process for the catalytic oxidation of propylene to acrylic acid the improvement comprising conducting the process in the presence of an effective amount of hydroquinone. The improved process is particularly applicable to the aqueous liquid phase reaction of propylene with molecular oxygen using a supported palladium catalyst.

8 Claims, No Drawings

PROCESS FOR THE CATALYTIC OXIDATION OF PROPYLENE TO ACRYLIC ACID

BACKGROUND OF THE INVENTION

The present invention relates to an improved process for the preparation of acrylic acid by the catalytic oxidation of propylene the improvement comprising conducting the process in the presence of an effective amount of hydroquinone.

In commercial processes it is important that the process be efficient and economical. This is especially important in catalytic processes and particularly in those processes employing expensive precious metal catalysts such as palladium. In general, a desirable catalytic process provides one or more of high catalyst utility, high product selectivity and low production of side products, particularly combustibles such as carbon dioxide.

The catalytic oxidation of propylene to acrylic acid is well known. See, for example, "Encylopedia of Chemical Technology", Second Edition, Kirk-Othmer, Vol. 1, pgs. 293–295 whereat the disclosed process involved the oxidation of propylene to hydroxypropionic acid using oxides of nitrogen or nitric acid as a catalyst for the reaction. Subsequent dehydration yields acrylic acid. Also see Chapter 10, e.g., pgs. 389–400, of "Propylene and its Industiral Derivatives", by E. G. Handcock, published by John Wiley, New York (1973). A detailed description of processes to produce acrylic acid is given in "Oxidation of Petrochemicals: Chemistry and Technology" by T. Dumas and W. Bulani, John Wiley & Sons, 1974. The Journal of Catalysis, Vol. 24, pgs. 173-177 (1972) shows the catalytic oxidation of olefins over metallic palladium catalysts suspended in water. Similarly, U.S. Pat. No. 3,624,147 shows a process for preparing acrylic acid by the liquid phase oxidation of propylene with molecular oxygen in the presence of water and a noble metal catalyst. U.S. Pat. No. 3,792,086 describes a process employing a catalyst composition containing phosphoric acid and palladium metal in the preparation of acrylic or methacrylic acid by the vapor phase oxidation of propylene or isobutylene, respectively. A number of U.S. patents directed to the preparation of such products are noted therein. U.S. Pat. No. 3,947,495 shows an improved catalyst composition containing a sulfur modifier. The references and patents noted in this paragraph are herein incorporated by reference.

U.S. Pat. No. 3,076,032 describes the $PdCl_2/CuCl_2$ redox oxidation of olefins to aldehydes, ketones and carboxylic acids such as acetic acid. Propylene is oxidized in such a system predominately to acetone and propionaldehyde as shown at column 6, lines 48–49 and quinones are utilized in this system to accelerate the oxidation of the redox system.

It is among the objects of the present invention to provide an improved process for the catalytic oxidation of propylene to acrylic acid.

Other objects and advantages of the invention will be apparent from the following detailed description.

SUMMARY OF THE INVENTION

It has now been found that the catalytic oxidation of propylene to acrylic acid is improved, surprisingly, by conducting the process in the presence of an effective amount of hydroquinone. The process is generally carried out with heterogeneous catalyst contact systems at elevated temperatures and may be used in vapor phase and liquid phase systems and also in mixed vapor-liquid phase systems which are sometimes called trickle phase or dropping phase systems.

The following description of preferred forms of the invention relates principally to the liquid phase system for the catalytic oxidation of propylene to acrylic acid. It will, however, be understood that the process described herein is similarly applicable to the other systems as set forth hereinabove and that such other latter embodiments are, therefore, also embraced within the scope of the present invention.

The following expressions are defined as follows and will be used throughout the disclosure.

The term "% $O_2$ Conversion" means $$\frac{\text{millimoles (MM) oxygen in} - \text{MM oxygen out}}{\text{MM oxygen in}} \times 100$$

The term "% Selectivity Component" means $$\frac{\text{MM component}}{\text{MM propylene reacted}} \times 100$$

The term "Catalyst Utility" means grams acrylic acid produced/gram catalyst metal/hour.

DESCRIPTION OF THE PREFERRED EMBODIMENTS

The solvent system is generally and, preferably, water, because of its availability and cost and excellent processing results are obtained. Other suitable solvents or water-solvent mixtures may be employed depending on the particular process employed.

The reaction temperature and pressure may vary within wide limits. In general, the reaction temperature is about 70° to 300° C., and preferably between about 90° to 150° C. It is highly preferred to maintain the reaction temperature above the critical point of propylene, to wit, about 91.8° C., to maintain the undissolved propylene as a gas.

The reaction pressure is generally between about 50 to 1000 pounds per $inch^2$ gauge (psig) and is preferably between about 100 and 600 psig. The reaction temperature and/or pressure have no critical upper limit but for technical and economic reasons, very high temperatures and pressures are not of interest. Low temperatures and pressures, while not excluded, are not normally used for this reaction.

Depending on the particular vapor phase or trickle phase system employed, the reaction temperature and pressure also may vary within wide limits. Generally, temperatures up to about 300° C., or higher and pressures up to about 300 psig, or higher, are employed. Usually the reaction temperature is about 50° to 200° C. and the pressure about atmospheric to 75 psig.

The relative proportions of propylene and oxygen may vary widely but for safety reasons explosive mixtures must be avoided. Oxygen rich mixtures containing 1% or less propylene may be employed, but in practice a large excess of propylene is usually used. In general, the mole ratio of propylene to oxygen is greater than about 3:1 and is preferably between about 5:1 to 10:1, e.g., about 8:1. Explosive mixtures may also be avoided by adding diluents such as nitrogen, carbon dioxide, methane, ethane and propane to the propylene/oxygen mixtures. It will be understood by those skilled in the art that when the oxygen is supplied in the form of air or other mixtures, that the proportions are suitably adjusted to maintain the desired proportion of propylene to oxygen. While the use of molecular oxygen is preferred, other oxidant systems are considered to be included within the broad scope of the invention.

Unsupported palladium metal may be employed as the catalyst, but usually the metal is dispersed on a powdered or pelletized support such as carbon, alumina, silica, silica-alumina, zirconia, glass beads, and the like. The preferred catalyst is palladium metal supported on a powdered carbon carrier having a particle size less than about 325 mesh (U.S. Series). Other catalytic metals, such as the noble metals, may be employed either alone or in combination, e.g., nickel, platinum and the like. The catalyst employed in the process may be prepared by known methods, e.g., contacting a metal salt solution with the support, drying and treating with a suitable reducing agent such as hydrogen, hydrazine, and the like.

In general, the palladium is employed in amounts of about 0.01% to 10%, preferably about 1% to 6%, e.g., 5%, by weight of the supported catalyst. The amount of supported catalyst is generally about 0.1% to 50%, preferably 1% to 15%, by weight of the reactants.

The process of this invention may be carried out continuously or discontinuously in any type of apparatus usually used for such a process.

The hydroquinone additive to the reaction mixture in an effective amount significantly improves the liquid phase catalytic oxidation process of propylene to acrylic acid. Other suitable benzenediol compounds and their derivatives may be employed such as pyrocatechol and resorcinol, with hydroquinone being preferred. A number of compounds are shown in Kirk-Othmer's Encyclopedia of Chemical Technology, Volume 11, pages 462-492, the disclosure of which is hereby incorporated by reference. The effective amount of hydroquinone may vary within wide limits and is generally about 0.01% to 10% based on the initial weight of the liquid reaction mixture. A preferred range is about 0.1% to 1.0%. In a vapor phase or trickle phase system, hydroquinone in an amount of about 0.1% to 50%, based on the catalyst weight, is generally employed. A preferred range is about 1% to 20%. Lower or higher amounts may be used and are not considered to be excluded from within the scope of the invention.

It is an important feature of the invention that the reaction mixture be substantially free of ions produced by highly ionizable compounds, e.g., salts such as the alkali and alkaline earth metal acetates and chlorides, potassium acetate, and others such as palladium chloride, copper chloride, copper acetate, ammonium chloride, etc., since the beneficial effect of the hydroquinone is markedly reduced, e.g., the amount of combustibles, such as $CO_2$, is increased and the catalyst utility is decreased. On a molar basis, an ion concentration of less than 0.1 M is desirable, preferably 0.01 M, or less. Correspondingly, amounts of the salt, e.g., potassium acetate, of about 1%, or more, by weight of the liquid reaction mixture, are to be avoided, with a preferred level being less than about 0.1%, e.g., 0.01%.

The following comparative example is given for purposes of illustration only and is not to be considered as constituting a limitation on the present invention.

EXAMPLE

A 300 milliliter (ml.) stainless steel autoclave (Autoclave Engineers Magnedrive) was used as the reactor vessel and identical conditions were employed for all the runs shown in Table I.

The reactor was charged with about 4 grams of a 5 weight percent palladium metal on powdered carbon catalyst having a particle size less than 325 mesh (U.S. Series). 100 ml. of water was added to the reactor followed by addition of the indicated amount of hydroquinone. After heating the reactor contents of about 100° C., a measured amount of liquid propylene was pumped into the reactor and vaporized to give a pressure of about 320 psig. 50 psig of oxygen was added to the reactor (total reactor pressure of about 370 psig) and the reaction started. The mole ratio of propylene to oxygen is about 8:1. The reactants were mixed using an Autoclave Engineers Dispersimax turbine stirrer. After a 15 minute time interval, the gaseous contents were vented, measured, and a gas sample taken for analysis while maintaining the reaction temperature. The propylene and oxygen were repressurized as indicated above, and the sequence repeated for a total of 9 cycles (total reaction time of 2.25 hours). At the end of the reaction time, the reactor was cooled to ambient temperature, and the reaction mixture quantitatively transferred to a filtering funnel where the catalyst was removed and washed. The filtrate was analyzed by gas chromatography and titration with standard base. The values of acrylic, propionic, and acetic acids as determined by gas chromatography were totalized and subtracted from the total acid content as determined by titration, to give the concentration of polymer. Trace components are not indicated and the results are shown hereinbelow in Table I.

TABLE I

| Run | Additive | % $O_2$ Conversion | % Selectivity | | | | | Utility gAA/gPd/hr[2] | wt % Acrylic Acid[3] |
|---|---|---|---|---|---|---|---|---|---|
| | | | Acrylic Acid | Acetic Acid | Acrolein | Polymer | $CO_2$ | | |
| 1 | None | 71.2 | 45.9 | 4.5 | 1.1 | 18.5 | 29.7 | 7.3 | 3.2 |
| 2 | 0.1 g (0.1%)[1] hydroquinone | 63.5 | 60.9 | 6.7 | 1.1 | 10.2 | 20.9 | 10.0 | 4.3 |
| 3 | 0.5 g (0.5%) hydroquinone | 74.2 | 65.4 | 7.4 | 1.7 | 6.0 | 19.0 | 11.1 | 4.7 |

[1]( ) = % by initial weight of the liquid reaction mixture.
[2]gAA/gPd/hr = grams Acrylic acid/gram palladium/hour.
[3]Final concentration in liquid reaction mixture.

The results clearly show the beneficial effect of conducting the process in the presence of an effective amount of hydroquinone. A comparison of the results shows a marked increase in the percent selectivity to acrylic acid and a marked decrease in the production of the combustible side product carbon dioxide. Also, the utility of the catalyst is significantly enhanced. The runs employing hydroquinone further provide a reaction mixture having a higher final concentration of acrylic acid, which is particularly beneficial in recovery operations.

While the process has been directed to the catalytic oxidation of propylene to acrylic acid, it will be understood that the process described herein is applicable to other unsaturated hydrocarbons, e.g., $C_2$–$C_8$ compounds such as isobutylene, 1-methyl-1-cyclopentene, and aromatic compounds such as toluene, and the like.

Various changes and modifications can be made in the process of this invention without departing from the spirit and scope thereof. The various embodiments disclosed herein were for the purpose of further illustrating the invention but were not intended to limit it.

I claim:

1. In a process for preparing acrylic acid by the liquid phase catalytic oxidation of propylene, the improvement for increasing the selectivity to acrylic acid, decreasing the production of the combustible side product carbon dioxide, enhancing the catalyst utility and providing a reaction mixture having a higher final concentration of acrylic acid which comprises conducting the process in the presence of an effective amount of hydroquinone.

2. A process according to claim 1 wherein the liquid phase is water.

3. A process according to claim 2 wherein the amount of hydroquinone is, by intial weight percent of the liquid reaction mixture, about 0.1% to 1.0%, and the oxidant is molecular oxygen.

4. A process according to claim 3 wherein the catalyst is palladium metal supported on a carrier.

5. A process according to claim 4 wherein the carrier is powdered carbon.

6. A process according to claim 3 wherein the mole ratio of propylene to oxygen to greater than about 3:1.

7. A process according to claim 3 wherein the reaction pressure is about 100 to 600 psig and the reaction temperature is about 90° to 150° C.

8. A process conducted according to claim 1 which is substantially free of ions.